(12) United States Patent
Kusaka et al.

(10) Patent No.: US 8,357,106 B2
(45) Date of Patent: Jan. 22, 2013

(54) ANALYSIS DEVICE

(75) Inventors: Yasuhide Kusaka, Kyoto (JP);
Hirokazu Matsuda, Kyoto (JP);
Yoshiharu Sato, Kyoto (JP)

(73) Assignee: Arkray, Inc., Kyoto (JP)

( * ) Notice: Subject to any disclaimer, the term of this patent is extended or adjusted under 35 U.S.C. 154(b) by 218 days.

(21) Appl. No.: 12/451,174

(22) PCT Filed: Apr. 29, 2008

(86) PCT No.: PCT/JP2008/058223
§ 371 (c)(1),
(2), (4) Date: May 12, 2010

(87) PCT Pub. No.: WO2008/136474
PCT Pub. Date: Nov. 13, 2008

(65) Prior Publication Data
US 2011/0040207 A1    Feb. 17, 2011

(30) Foreign Application Priority Data
Apr. 29, 2007   (JP) .................................. 2007-120397

(51) Int. Cl.
*A61B 5/00* (2006.01)
(52) U.S. Cl. ........................................ 600/583; 600/584
(58) Field of Classification Search .................. 600/583, 600/584
See application file for complete search history.

(56) References Cited

U.S. PATENT DOCUMENTS

| | | |
|---|---|---|
| 5,320,732 A | 6/1994 | Nankai et al. |
| 5,783,821 A | 7/1998 | Costello, Jr. |
| 6,233,269 B1 | 5/2001 | Lohrding et al. |
| 2002/0198444 A1 | 12/2002 | Uchigaki et al. |
| 2005/0224345 A1 | 10/2005 | Taniike et al. |

FOREIGN PATENT DOCUMENTS

| | | |
|---|---|---|
| JP | 04-314482 A | 11/1992 |
| JP | 08-010208 B2 | 1/1996 |
| JP | 2003-265444 A | 9/2003 |
| JP | 2004-101514 A | 4/2004 |
| JP | 2006-015068 A | 1/2006 |
| TW | 2006-30071 | 9/2006 |
| WO | WO-01/41643 A1 | 6/2001 |

OTHER PUBLICATIONS

International Search Report mailed on Sep. 2, 2008.
Office Action in Taiwanese Patent Application No. 097115753, dated Feb. 4, 2012.
Notice of Examination Report from Taiwanese Patent Office for application No. 097115753 dated Aug. 16, 2011 (w/English translation).
Office Action in Taiwanese Patent Application No. 097115753, dated Jul. 26, 2012.

*Primary Examiner* — Brian Szmal
*Assistant Examiner* — Emily Lloyd
(74) *Attorney, Agent, or Firm* — Rader, Fishman & Grauer PLLC

(57) ABSTRACT

This invention is regard to an analysis device that analyze a specific component in bodily fluid extracted from the skin using an analysis tool. The analysis device comprise a laser beam oscillation section that emits a laser beam for extracting the bodily fluid from the skin, and a detection mechanism that detects whether or not the analysis tool exists at a target position. The analysis device is adapted to emit the laser beam from the laser beam oscillation section when the analysis tool is detected by the detection mechanism.

15 Claims, 6 Drawing Sheets

FIG.6
FIG.6A
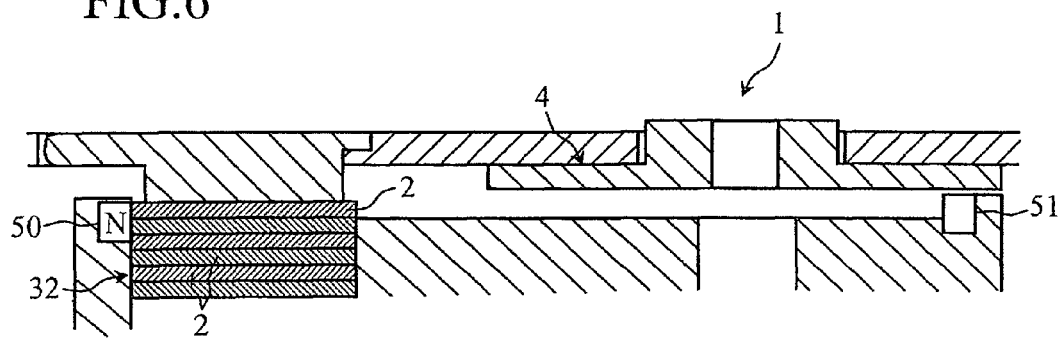
FIG.6B
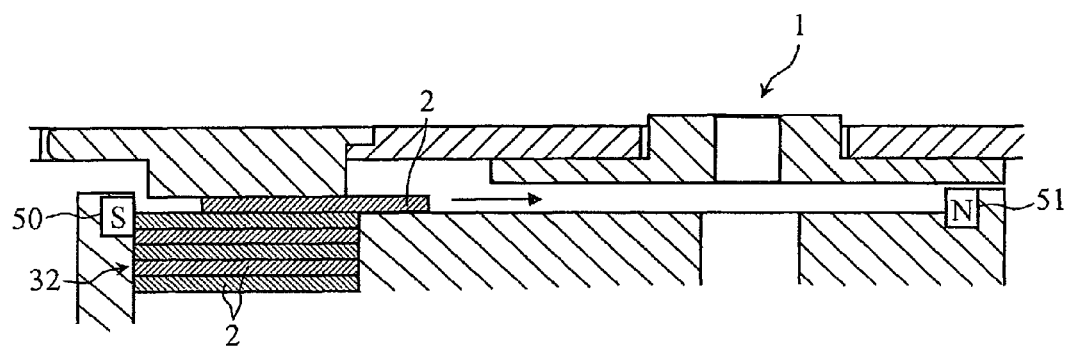
FIG.6C
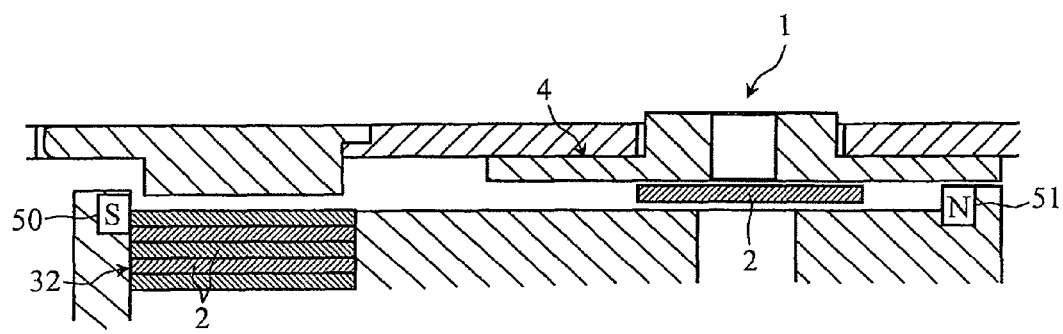

FIG.7
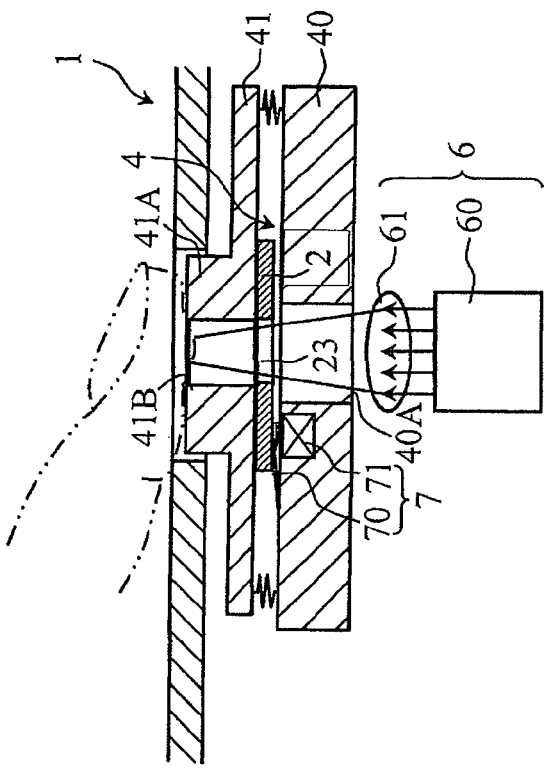
FIG.7A
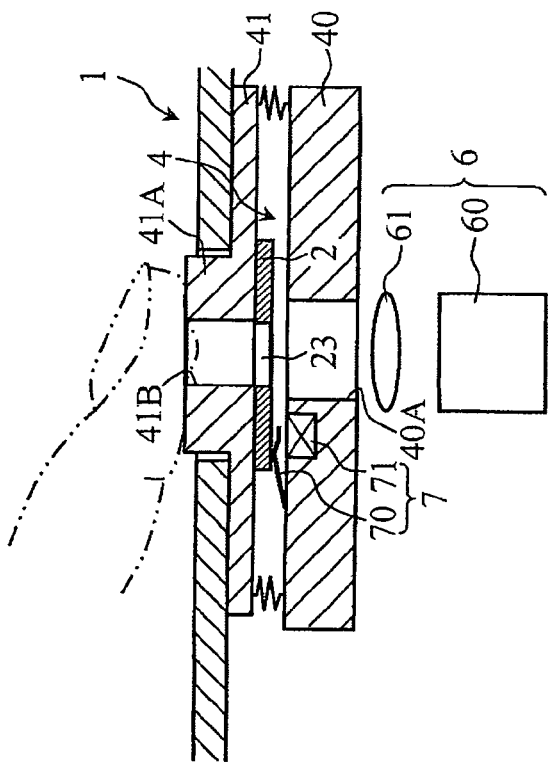
FIG.7B

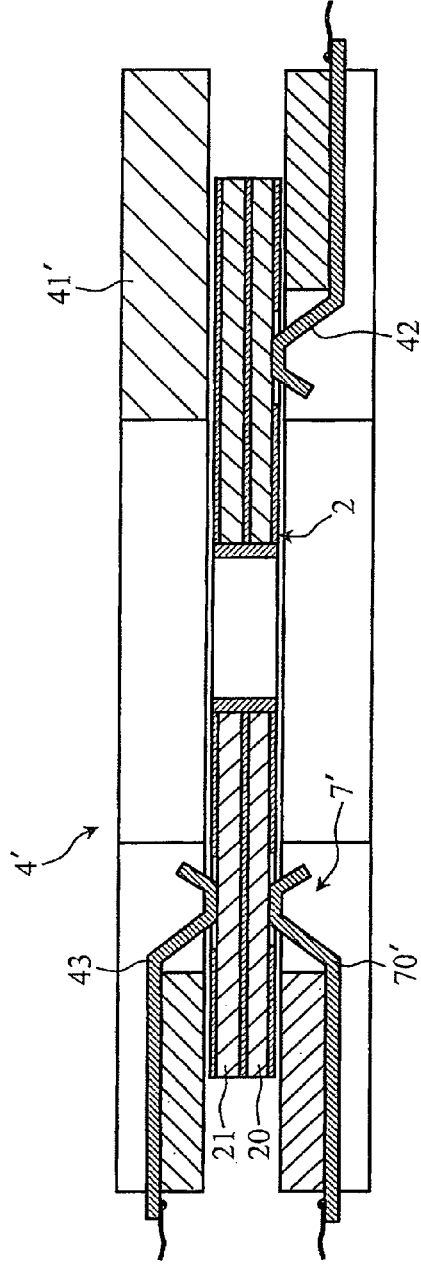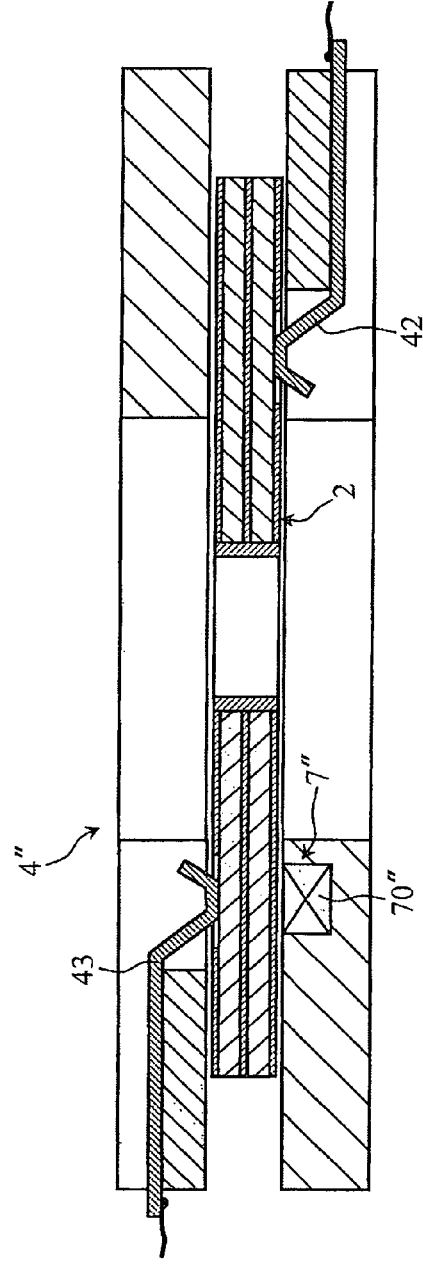

ANALYSIS DEVICE

TECHNICAL FIELD

The present invention relates to an analysis device that analyze a specific component (such as glucose, cholesterol and lactic acid) in the bodily fluid extracted from a skin by emission of laser beam.

RELATED ART

When measuring concentration of glucose or the like in blood, a method of using a single-use analysis tool is employed as a simple method (see patent document 1, for example). As the analysis tool, there is one capable of carrying out analysis electrochemically or optically.

A sample, such as blood can be obtained by incising a skin using a lancet, for example. It is general to prick a skin with a puncture needle as the lancet, but there is also a lancet capable of extracting the blood from a skin by emitting the skin with laser beam (see patent document 2, for example).

According to a general laser lancet, a user operates a separately provided laser beam emitting button in a state in which a laser emitting opening is pushed against a skin, such that the laser beam is emitted.

According to this conventional lancet, however, if a user erroneously operates the button even in a state in which the laser emitting opening is not pushed against a skin, laser beam is emitted. Since the laser beam has enough energy to make the bodily fluid extracted from a skin, it is not preferable that laser beam is emitted unintentionally.

Patent Document 1: Japanese Patent Publication No. H8-10208
Patent Document 2: Japanese Patent Application Laid-open No. H4-314482

DISCLOSURE OF THE INVENTION

Problem to be Solved by the Invention

It is an object of the present invention to prevent laser beam from being erroneously emitted.

Method of Solving the Problem

The present invention provides an analysis device that analyzes a specific component in bodily fluid extracted from the skin using an analysis tool. The analysis device comprises an extraction mechanism that extracts the bodily fluid from the skin, and a detection mechanism that detects whether or not the analysis tool exists at a target position. The extraction mechanism is activated when the analysis tool is detected by the detection mechanism.

The detection mechanism includes a switch that is turned ON when the analysis tool exists at the target position, and the extraction mechanism is activated when the switch is turned ON.

The analysis device according to the invention may further include a moving portion capable of moving together with the analysis tool. In this case, it is preferable that the switch is turned ON by moving the moving portion in a state in which the analysis tool exists at the target position.

The detection mechanism further includes an elastic member that contacts the switch when the moving portion is moved.

The analysis tool includes a plurality of electrodes capable of electrochemically carrying out an analysis of a sample. In this case, the detection mechanism may include a pair of detection terminals that contact the plurality of electrodes and detect the analysis tool depending upon whether or not the pair of detection terminals are in a short-circuited state. It is preferable that the pair of detection terminals are brought into the short-circuited state from an open state by moving the moving portion in a state in which the analysis tool exists at the target position.

The moving portion is moved by a load that is externally input. The moving portion may include a pass-through portion that allows the pricking element to pass therethrough.

The detection mechanism optically may detect a specific portion of the analysis tool.

It is preferable that the extraction mechanism is capable of emitting a laser beam to irradiate the skin, and emits the laser beam when the analysis tool is detected by the detection mechanism.

BRIEF DESCRIPTION OF THE DRAWINGS

FIGS. 6A to 6C are sectional views showing an essential portion for explaining a sensor supply mechanism in the analysis device shown FIG. 1.

FIGS. 7A and 7B are sectional views showing an essential portion for explaining a sensor detection mechanism in the analysis device shown FIG. 1.

FIGS. 8A and 8B are sectional views showing an essential portion for explaining another example of the sensor detection mechanism.

BEST MODE OF IMPLEMENTING THE INVENTION

An analysis device according to the present invention will be described with reference to the drawings.

Figure 1:
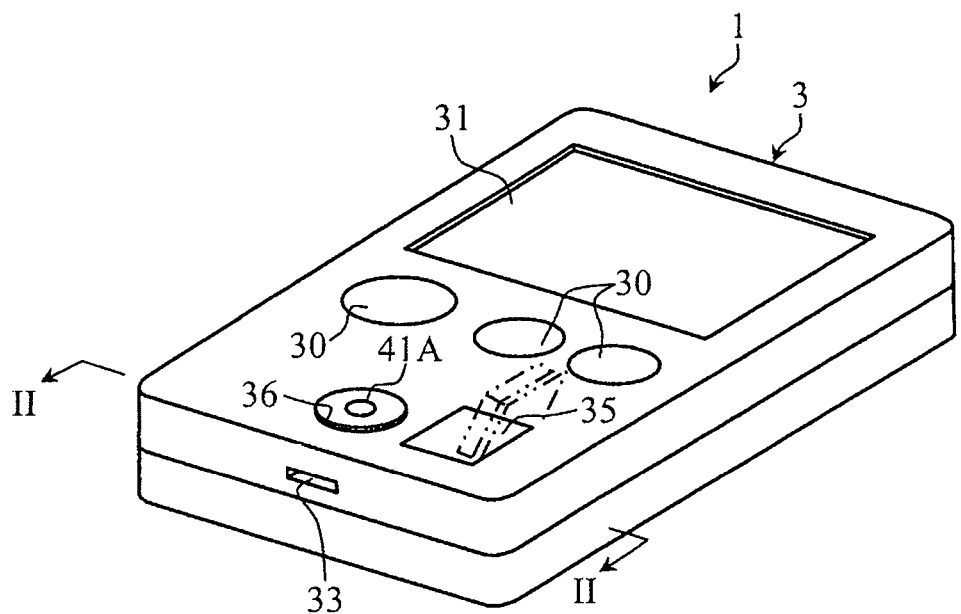
FIG. 1 is an overall perspective view showing an example of an analysis device according to the present invention.
Figure 2:
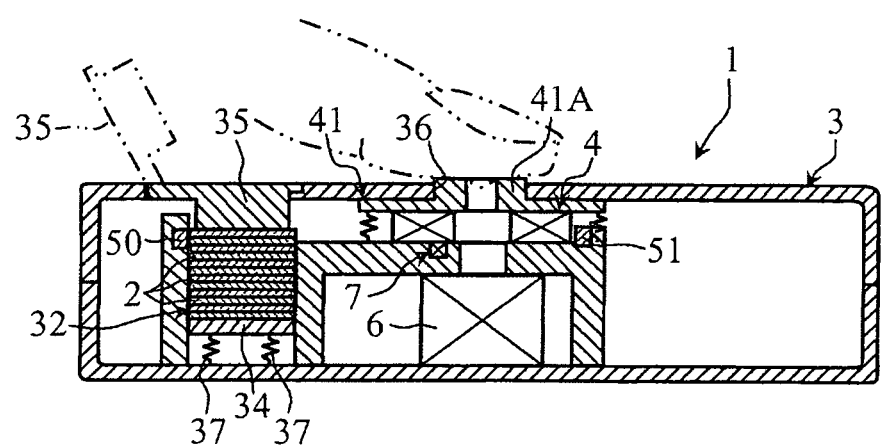
FIG. 2 is a sectional view taken along the line II-II in FIG. 1.

An analysis device 1 shown in FIGS. 1 and 2 is for analyzing a sample by an electrochemical method using biosensors 2. The analysis device 1 is constituted as a portable type apparatus that can be carried. The analysis device 1 accommodates therein a plurality of biosensors 2, and includes a casing 3, a connector 4, a sensor supply mechanisms 50 and 51, a laser beam oscillation mechanism 6 and a sensor detection mechanism 7.

Figure 3:
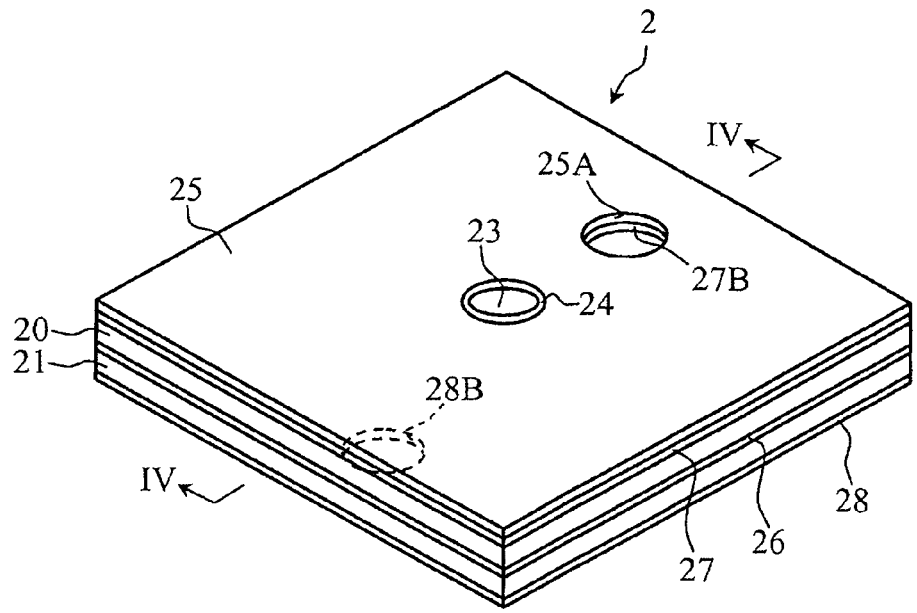
FIG. 3 is an overall perspective view showing an example of biosensor used for the analysis device shown in FIG. 1.
Figure 4:
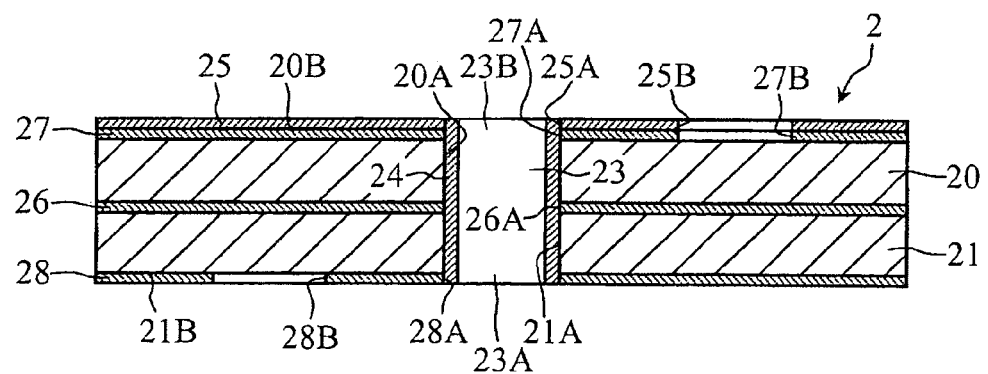
FIG. 4 is a sectional view taken along the line IV-IV in FIG. 3.

As shown in FIGS. 3 and 4, the biosensors 2 are constituted as single-use biosensors. The biosensors 2 are used for analyzing a specific component (such as glucose, cholesterol and lactic acid) in bodily fluid such as blood and interstitial fluid. The biosensor 2 is formed into a rectangular plate-like shape as a whole, and has a size of (2 to 10 mm)*(2 to 10 mm)*(0.5 to 2 mm), for example. The biosensor 2 includes an operation electrode 20 and a counter electrode 21 which are laminated on each other, and further includes a capillary 23, a reagent layer 24 and a heating layer 25.

The operation electrode 20 and the counter electrode 21 apply voltage to bodily fluid introduced into the capillary 23, and are used to measure response current at this time. The operation electrode 20 and the counter electrode 21 include through holes 20A and 21A and are formed into the same or almost the same shape. The through holes 20A and 21A define the capillary 23, and are formed into a circle having a diameter of 0.2 to 1 mm at central portions of the operation electrode 20 and the counter electrode 21. The operation electrode 20 and the counter electrode 21 are made of conductive magnetic material such as nickel, and formed into a size of (2 to 10 mm)*(2 to 10 mm)*(0.2 to 1 mm).

An insulation layer 26 is interposed between the operation electrode 20 and the counter electrode 21, and the operation electrode 20 and the counter electrode 21 are bonded to each other via the insulation layer 26. A through hole 26A defining the capillary 23 is formed in a central portion of the insulation layer 26, and a thickness of the insulation layer 26 is formed into 20 to 100 μm by a known hot-melt sheet. A diameter of the through hole 26A is the same or almost the same as those of the through holes 20A and 21A of the operation electrode 20 and the counter electrode 21.

Insulation layers 27 and 28 are formed on surfaces 20B and 21B of the operation electrode 20 and the counter electrode 21. These insulation layers 27 and 28 are for restraining bodily fluid from adhering to the surfaces 20B and 21B of the operation electrode 20 and the counter electrode 21. The insulation layers 27 and 28 also have through holes 27A and 28A like the insulation layer 26 by a known hot-melt sheet. Diameters of the through holes 27A and 28A are the same or almost the same as those of the through holes 20A and 21A of the operation electrode 20 and the counter electrode 21. The insulation layers 27 and 28 are formed with holes 27B and 28B from which the surface 20B or 21B of the operation electrode 20 or the counter electrode 21 is exposed. Later-described measuring terminals 42 and 43 (see FIG. 5) of the connector 4 can contact the operation electrode 20 or the counter electrode 21 through the holes 27B and 28B.

The capillary 23 is for moving bodily fluid introduced from an opening 23A toward an opening 23B using capillary action and for holding the bodily fluid therein. The capillary 23 allows laser beam to enter from the later-described laser beam oscillation mechanism 6 (see FIG. 5). The capillary 23 is defined by the through holes 20A, 21A and 26A to 28A of the operation electrode 20, the counter electrode 21 and the insulation layers 26 to 28. The volume is set to 0.03 to 10 μL, for example.

The reagent layer 24 includes reagents required for analyzing the specific component in bodily fluid, and covers an inner surface of the capillary 23. The reagent layer 24 includes an electron transport material and an oxyreductase, and is formed into a solid object which easily melts in bodily fluid. Therefore, when bodily fluid is introduced into the capillary 23, the reagent layer 24 melts, and a liquid-phase reaction system including the electron transport material, the oxyreductase and the bodily fluid is constituted in the capillary 23.

Material as the oxyreductase is selected depending upon kinds of the specific component to be analyzed. For example, when glucose is to be analyzed, glucose dehydrogenase (GDH) or glucose oxidase (GOD) can be used. Material as the electron transport material, ruthenium complex or iron complex can be used. Typically, $[Ru(NH_3)_6]Cl_3$ or $K_3[Fe(CN)_6]$ can be used.

The heating layer 25 is for adjusting a temperature of the liquid-phase reaction system in the capillary 23, and covers substantially the entire insulation layer 27. The heating layer 25 has a through hole 25A and a hole 25B. The through hole 25A is in communication with the through hole 27A of the insulation layer 27, and the hole 25B is in communication with the hole 27B of the insulation layer 27. The entire heating layer 25 is made of resistance material. As the resistance material, various know materials such as iron-chromium-aluminum-based materials and nickel-chromium-based materials can be used.

It is not always necessary that the heating layer 25 covers substantially the entire surface 20A of the operation electrode 20, and the heating layer 25 may be provided by pattern-forming a bellows wiring.

The casing 3 shown in FIGS. 1 and 2 defines an outward appearance of the analysis device 1, and includes a plurality of operation buttons 30, a display panel 31, a sensor accommodating portion 32 and a waste vent 33. The plurality of operation buttons 30 produce signals for carrying out the analysis operation, and for carrying out various setting operations (such as setting of analysis condition and inputting of ID of a subject). An analysis result, an error, operating procedure and an operating status at the time of setting operation are displayed on the display panel 31. The plurality of biosensors 2 are laminated and accommodated in the sensor accommodating portion 32. The sensor accommodating portion 32 includes a mounting portion 34 and a lid 35 which can open and close. The mounting portion 34 is biased by a coil spring 37 upward (toward the lid 35). A biosensor 2 that was used for analysis is discarded from the analysis device 1 through the waste vent 33.

Figure 5:
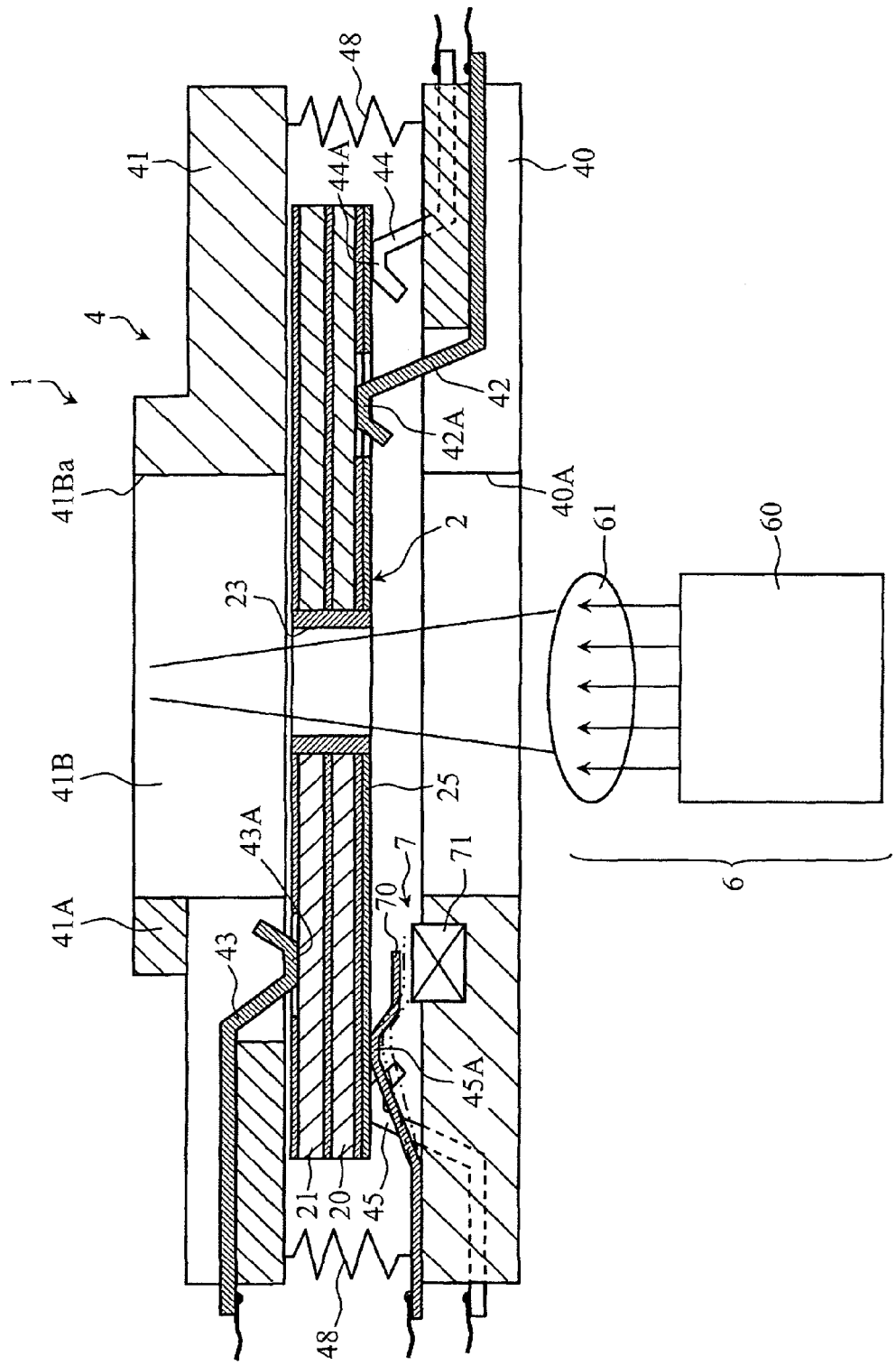
FIG. 5 is a sectional view showing an essential portion for explaining a connector and a laser beam oscillation mechanism in the analysis device shown in FIG. 1.

As shown in FIG. 5, the connector 4 holds the biosensor 2, and applies voltage between the operation electrode 20 and the counter electrode 21 of the biosensor 2 or applies to the heating layer 25. The connector 4 includes a fixed body 40, a movable body 41, the measuring terminals 42 and 43 and heating terminals 44 and 45.

The fixed body 40 is for supporting the measuring terminal 42 and the heating terminals 44 and 45, and includes a through hole 40A. The through hole 40A allows the laser beam to enter from the laser beam oscillation mechanism 6. The later-described sensor detection mechanism 7 (elastic body 70 and switch 71) is disposed in the fixed body 40.

The movable body 41 supports the measuring terminal 43. The movable body 41 is connected to the fixed body 40 through a coil spring 48. The movable body 41 is biased upward and the movable body 41 can vertically move. The movable body 41 includes a convex portion 41A and a through hole 41B. A skin such as a fingertip is pushed against the convex portion 41A when collecting bodily fluid, and the convex portion 41A is exposed from a through hole 36 (see FIG. 1) of the casing 3. That is, if a skin such as a fingertip is pushed against the convex portion 41A, the movable body 41 is moved downward. The through hole 41B allows laser beam to enter from the laser beam oscillation mechanism 6. The through hole 41B continuously extends to the convex portion 41A, and is in communication with outside of the apparatus at an end surface of the convex portion 41A. That is, the opening 41Ba of the through hole 41B functions as a bodily fluid collecting opening.

The terminals 42 to 45 are constituted as leaf springs. The measuring terminals 42 and 43 are for applying voltage between the operation electrode 20 and the counter electrode 21 of the biosensor 2. The measuring terminal 42 contacts the operation electrode 20, and a contact 42A projects upward. The measuring terminal 43 contacts the counter electrode 21, and a contact 43A projects downward. The heating terminals 44 and 45 apply voltage to the heating layer 25 of the biosensor 2 to heat the heating layer 25. The contacts 44A and 45A of the heating terminals 44 and 45 project upward, and contact the heating layer 25.

In the connector 4, the contacts 42A, 44A and 45A of the measuring terminal 42 constituted as a leaf spring and the heating terminals 44 and 45 project upward from the fixed body 40, and the contact 43A of the measuring terminal 43 projects downward from the movable body 41. Therefore, in the connector 4, the biosensor 2 can be held between the fixed body 40 and the movable body 41.

As shown in FIGS. 6A to 6C, the sensor supply mechanisms 50 and 51 supply, to the connector 4, the uppermost one of the plurality of biosensors 2 laminated on the sensor accommodating portion 32. The sensor supply mechanisms 50 and 51 include electromagnets 50 and 51, respectively. The electromagnet 50 is provided adjacent to the sensor accommodating portion 32, and the electromagnet 51 is provided adjacent to the connector 4. The electromagnet 50 magnetizes the biosensor 2, and applies repulsion between the magnetized biosensor 2 and the electromagnet 50. The electromagnet 51 applies an attraction between the magnetized biosensor 2 and the electromagnet 51.

As shown in FIGS. 7A and 7B, when extracting the bodily fluid such as blood from a skin, the laser beam oscillation mechanism 6 emits the laser beam to irradiate the skin. The laser beam oscillation mechanism 6 includes a laser beam oscillator 60 such as a laser diode and a condensing lens 61.

As shown in FIGS. 5, 7A and 8B, the sensor detection mechanism 7 is for detecting whether or not the biosensor 2 exists at a target position of the connector 4, and includes the elastic body 70 and the switch 71. The elastic body 70 is fixed to the fixed body 40 in the connector 4, and is short-circuited with the switch 71. The elastic body 70 turns the switch 71 ON when the movable body 41 (biosensor 2) moves downward. The switch 71 is for turning predetermined motion of the analysis device 10N and OFF. When the switch 71 is ON, the switch 71 controls the laser beam oscillator 60 and emits laser beam.

The elastic body 70 may be fixed to the movable body 41. The elastic body 70 may have elasticity due to a shape other than a leaf spring or properties of material.

Next, operation of the analysis device 1 will be described.

As shown in FIGS. 6A to 6C, in the analysis device 1, when a plurality of biosensors 2 are set in the sensor accommodating portion 32 or when analysis is completed, the biosensors 2 are supplied to the connector 4 from the sensor accommodating portion 32 by the sensor supply mechanisms 50 and 51.

More specifically, in the sensor supply mechanisms 50 and 51, as shown in FIG. 6A, the biosensor 2 is magnetized by the electromagnet 50. In the illustrated example, in the electromagnet 50, the N pole is adjacent to the biosensor 2, while a side of the biosensor 2 close to the electromagnet 50 is magnetized with the S pole and a side of the biosensor 2 farther from the electromagnet 50 is magnetized with the N pole. At this time, no magnetic pole is generated in the electromagnet 51.

Next, as shown in FIGS. 6B and 6C, the polarity of the electromagnet 50 is reversed and repulsion is generated between the biosensor 2 and the electromagnet 50. On the other hand, polarity is generated in the electromagnet 51, and an attraction is generated between the biosensor 2 and the electromagnet 51 which has a reverse polarity to the electromagnet 50. In this way, the biosensor 2 is moved toward the connector 4 by the repulsion of the electromagnet 50 and the attraction by the electromagnet 51.

As shown in FIG. 5, in the connector 4, terminals 42 to 45 constituted as the leaf springs project from the fixed body 40 and the movable body 41 and thus, a load for sandwiching the biosensor 2 is applied to the connector 4. On the other hand, as shown in FIGS. 3 and 4, in the biosensor 2, the holes 27B and 28B are formed in the insulation layers 27 and 28 through which the operation electrode 20 and the counter electrode 21 are exposed. Therefore, the movement of the biosensor 2 is stopped by the step between the holes 27A and 28B. At this time, the measuring terminal 42 of the connector 4 contacts the operation electrode 20, the measuring terminal 43 contacts the counter electrode 21, and the heating terminals 44 and 45 contacts the heating layer 25.

While a detection mechanism for detecting that the biosensor 2 is mounted on the connector 4 is provided, when the biosensor 2 is detected by the detection mechanism, polarities may not be generated in the electromagnets 50 and 51, and movement of the biosensor 2 may be stopped. The detection mechanism in this case may employ a configuration whereby voltage is applied between the heating terminals 44 and 45 in the connector 4, and current-carrying states of the heating terminals 44 and 45 are checked.

The sensor supply mechanisms 50 and 51 are not limited to items having the electromagnets 50 and 51, and, for example, a known actuator may be used. In this case, in the biosensor 2, it is not always necessary that the operation electrode 20 and the counter electrode 21 are made of magnetic material.

As shown in FIGS. 7A and 7B, when analysis of a specific component in bodily fluid is to be carried out using the analysis device 1, skin such as that of a fingertip is pushed against the convex portion 41A of the movable body 41, and the movable body 41 is moved downward. Due to this, the elastic body 70 in the sensor detection mechanism 7 is moved downward together with the movable body 41 (biosensor 2). As the elastic body 70 moves downward, the elastic body 70 turns the switch 71 ON, and the power supply of the analysis device 1 is turned ON. At this time, a laser beam is emitted from the laser beam oscillation mechanism 6.

The biosensor 2 includes the capillary 23. The fixed body 40 and the movable body 41 include through holes 40A and 41B. Thus, skin placed on the convex portion 41A is irradiated with the laser beam emitted from the laser beam oscillator 60. When the skin is irradiated with the laser beam, bodily fluid such as blood is extracted from the skin. At this time, since the skin is pushed against the convex portion 41A, the skin is congested, and phenomenon of extraction of bodily fluid such as blood is accelerated.

Bodily fluid from the skin is introduced into the capillary 23 by capillary action generated in the capillary 23 of the biosensor 2. The reagent layer 24 is melted in the capillary 23, and the liquid-phase reaction system is constituted.

When the switch 71 is turned ON, as shown in FIG. 5, voltage is applied between the measuring terminals 42 and 43 in the connector 4 and between the heating terminals 44 and 45. If voltage is applied between the heating terminals 44 and 45, the heating layer 25 is heated. Heat of the heating layer 25 is transmitted to the operation electrode 20 and the counter electrode 21, and bodily fluid introduced into the capillary 23 is heated. Due to this, the bodily fluid in the capillary 23 is heated to a target temperature.

As a result of voltage being applied between the measuring terminals 42 and 43 and between the heating terminals 44 and 45, voltage is applied between the operation electrode 20 and the counter electrode 21, such that voltage is also applied to the liquid-phase reaction system. Due to this, a specific component such as glucose in the bodily fluid is reduced (electrons are taken out) by oxyreductase, and the electrons are supplied to the operation electrode 20 through the electron transport material. An amount of the electrons supplied to the operation electrode 20 is measured as response current through the measuring terminals 42 and 43. In the analysis device 1, concentration of the specific component such as glucose is calculated based on the response current. The result of the calculation is displayed on the display panel 31 shown in FIG. 1.

When the analysis of bodily fluid is completed, used biosensor 2 is discarded through the waste vent 33. The biosensor 2 may be discarded automatically by a discarding mechanism provided in the analysis device 1 or a user may discard the biosensor 2 manually by operating a lever. When a used biosensor 2 is discarded, a new biosensor 2 is supplied to the connector 4 by the sensor supply mechanisms 50 and 51.

In the analysis device 1, bodily fluid extracted from the skin by the laser beam is supplied to the biosensor 2 in its intact collected state. Therefore, separate apparatuses for collecting bodily fluid and for analyzing the bodily fluid are unnecessary, and blood can easily be sucked by the biosensor 2, and the burden on a user is reduced.

The analysis device 1 is constituted such that the switch 71 is turned ON when skin is pushed against the convex portion 41A of the movable body 41 in the connector 4 in a state in which the biosensor 2 is held by the connector 4. Therefore, since a laser beam is only emitted while the convex portion 41A is moved by the skin, it is possible to prevent the laser beam from being emitted unintentionally. According to this configuration in which the switch 71 is turned ON due to pushing by the skin, since a necessary circuit can only be operated only while skin is pushed, power consumption can be suppressed and running costs can be reduced.

It is not always necessary to use a biosensor 2 that is previously accommodated in the analysis device 1, and the biosensor 2 can be mounted on the connector 4 in the analysis device 1 at the time of analysis.

Next, another example of the sensor detection mechanism will be described with reference to FIGS. 8A and 8B. In FIGS. 8A and 8B, the same elements as the analysis device 1 and the biosensors 2 explained previously with the numeral references to FIGS. 1 to 7 are designated with the same numeral references, and redundant explanation will be omitted below.

A sensor detection mechanism 7' shown in FIG. 8A is provided with a detection terminal 70' in the connector 4' in addition to the measuring terminals 42 and 43. The detection terminal 70' is brought into contact with the operation electrode 20 of the biosensor 2. That is, the detection terminal 70' can detect that the biosensor 2 is supplied to the connector 4' by detecting whether or not the detection terminal 70' and the measuring terminal 42 are short-circuited through the operation electrode 20. The measuring terminal 42 in this case also functions as a detection terminal.

The sensor detection mechanism 7' may be constituted such that the upper block 41' in the connector 4' can move, so that the block 41' is moved downward and as a result the detection terminal 70' contacts the operation electrode 20. Further, the sensor detection mechanism 7' may be constituted such that the biosensor 2 is mounted on the connector 4' so that the detection terminal 70' contacts the operation electrode 20.

Short circuit between the detection terminal and the measuring terminal 43 may be detected using the counter electrode 21. Further, a pair of detection terminals which are used only for detection may be provided in addition to the measuring terminals 42 and 43, and short circuit between these detection terminals may be detected using the operation electrode 20 and the counter electrode 21.

A sensor detection mechanism 7" shown in FIG. 8B detects that a biosensor 2 is supplied to a connector 4" by an optical technique. The connector 4" is provided with an optical sensor 70" such as a photosensor, and it is possible to detect that a biosensor 2 is supplied to the connector 4" by recognizing a predetermined location of the biosensor 2 by the optical sensor 70".

The sensor detection mechanisms 7' and 7" shown in FIGS. 8A and 8B can employ a configuration whereby when it is detected that a biosensor 2 is supplied to the connector 4', 4", laser beam can be emitted from the laser beam oscillation mechanism 6 (see FIG. 7). That is, the laser beam is not emitted from the laser beam oscillation mechanism 6 as long as a biosensor 2 is not mounted on the connector 4', 4", so that the laser beam is prevented from being emitted erroneously.

The present invention is not limited to the above-described embodiment and can variously be codified. For example, the invention can also be applied to an analysis tool such as a biosensor having a operation electrode and a counter electrode provided on an insulative substrate or a biosensor which carries out analysis of bodily fluid by colorimetry.

Further, the present invention is not limited to the analysis device having the extraction mechanism such as the laser beam oscillator, and the invention can also be applied to an analysis device having a configuration whereby a puncture needle is activated to insert a needle into a skin for extracting the bodily fluid from the skin.

The invention claimed is:

1. An analysis device adapted to analyze a specific component in bodily fluid extracted from skin and operative in conjunction with an analysis tool, the analysis device comprising:
   an extraction mechanism configured to extract the bodily fluid from the skin,
   a detection mechanism configured to detect whether the analysis tool is located at a target position, and
   an analyzing element configured to analyze the specific component in the bodily fluid extracted from the skin,
   wherein the extraction mechanism is configured to activate when the analysis tool is detected by the detection mechanism as located at the target position.

2. The analysis device according to claim 1, wherein the detection mechanism comprises a switch configured to turn ON when the analysis tool is located at the target position, and the extraction mechanism is configured to activate when the switch is turned ON.

3. The analysis device according to claim 2, further comprising a moving portion capable of moving together with the analysis tool, wherein the switch is configured to be turned ON by movement of the moving portion to where the analysis tool is located at the target position.

4. The analysis device according to claim 3, wherein the moving portion is configured to move by applying an external force thereto.

5. The analysis device according to claim 3, wherein the detection mechanism further comprises an elastic member that is configured to contact the switch when the moving portion is moved to where the analysis tool is located at the target position.

6. The analysis device according to claim 3, wherein:
   the extraction mechanism comprises a pricking element for pricking the skin; and
   the moving portion comprises a pass-through portion that is sized to allow the pricking element to pass therethrough.

7. The analysis device according to claim 1, wherein the detection mechanism is configured to optically detect a specific portion of the analysis tool.

8. The analysis device according to claim 1, wherein the extraction mechanism is capable of emitting a laser beam to irradiate the skin, and is configured to emit the laser beam when the analysis tool is detected by the detection mechanism as being located at the target position.

9. An analysis apparatus, comprising:
an analysis tool including a plurality of electrodes;
an analysis device configured to analyze a specific component in bodily fluid extracted from skin and operative in conjunction with the analysis tool, the analysis device including an extraction mechanism configured to extract the bodily fluid from the skin and a detection mechanism configured to detect whether the analysis tool is located at a target position; and
an analyzing element configured to analyze the specific component in the bodily fluid extracted from the skin,
wherein the extraction mechanism is configured to activate when the analysis tool is detected by the detection mechanism as located at the target position.

10. The analysis apparatus according to claim 9, wherein:
the detection mechanism comprises a pair of detection terminals that are configured to contact the plurality of electrodes and to detect the analysis tool when the pair of detection terminals contact the plurality of electrodes.

11. The analysis apparatus according to claim 10, further comprising a moving portion capable of moving together with the analysis tool, and the pair of detection terminals are configured to contact the plurality of electrodes when the moving portion is moved to where the analysis tool is located at the target position.

12. The analysis apparatus according to claim 11, wherein the moving portion is configured to move by applying an external force thereto.

13. The analysis apparatus according to claim 11, wherein the extraction mechanism comprises a pricking element for pricking the skin, and the moving portion comprises a pass-through portion sized to allow the pricking element to pass therethrough.

14. The analysis apparatus according to claim 9, wherein the detection mechanism is configured to optically detect a specific portion of the analysis tool.

15. The analysis apparatus according to claim 9, wherein the extraction mechanism is capable of emitting a laser beam to irradiate the skin, and is configured to emit the laser beam when the analysis tool is detected by the detection mechanism as located at the target position.

* * * * *